(12) United States Patent
Kim et al.

(10) Patent No.: US 7,991,470 B2
(45) Date of Patent: *Aug. 2, 2011

(54) POST-SHOCK RECOVERY MONITORING FOR TACHYARRHYTHMIA DISCRIMINATION

(75) Inventors: Jaeho Kim, Redmond, WA (US); Joseph M. Bocek, Seattle, WA (US); Eric G. Lovett, Roseville, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 666 days.

This patent is subject to a terminal disclaimer.

(21) Appl. No.: 12/056,684

(22) Filed: Mar. 27, 2008

(65) Prior Publication Data

US 2008/0177340 A1  Jul. 24, 2008

Related U.S. Application Data

(62) Division of application No. 10/746,857, filed on Dec. 24, 2003, now Pat. No. 7,353,062.

(51) Int. Cl.
*A61N 1/365* (2006.01)

(52) U.S. Cl. .................................................. 607/14

(58) Field of Classification Search ............... 607/4, 5, 607/14
See application file for complete search history.

(56) References Cited

U.S. PATENT DOCUMENTS

| | | | |
|---|---|---|---|
| 5,207,219 A | 5/1993 | Adams et al. | |
| 5,251,626 A | 10/1993 | Nickolls et al. | |
| 6,223,078 B1 | 4/2001 | Marcovecchio | |
| 6,449,503 B1 | 9/2002 | Hsu | |
| 6,636,764 B1 | 10/2003 | Fain et al. | |
| 7,107,098 B2 | 9/2006 | Sharma et al. | |
| 7,353,062 B2 | 4/2008 | Kim et al. | |
| 2003/0144700 A1 | 7/2003 | Brown et al. | |
| 2005/0149125 A1 | 7/2005 | Kim et al. | |

FOREIGN PATENT DOCUMENTS

| | | |
|---|---|---|
| EP | 0469817 A2 | 2/1992 |
| WO | WO-03047690 A2 | 6/2003 |

OTHER PUBLICATIONS

"U.S. Appl. No. 10/746,857, Response filed Oct. 5, 2006 to Non-Final Office Action mailed Jul. 5, 2007", 12 pgs.
"U.S. Appl. No. 10/746,857, Response filed Jul. 25, 2007 to Final Office Action mailed May 25, 2007", 11 pgs.
"Final Office Action Mailed May 25, 2007 in U.S. Appl. No. 10/746,857", 9 pgs.
"International Search Report for corresponding PCT Application No. PCT/US2004/042196",(Apr. 15, 2005),4 pgs.

(Continued)

*Primary Examiner* — Scott M Getzow
*Assistant Examiner* — Amanda Patton
(74) *Attorney, Agent, or Firm* — Schwegman, Lundberg & Woessner, P.A.

(57) ABSTRACT

A cardiac rhythm management device is configured to discriminate between ventricular and supraventricular tachycardias (referred to as SVT/VT discrimination) by utilizing a morphology criterion in which the morphology of electrogram waveforms during ventricular beats are analyzed to determine if the beats are normally conducted. After the delivery of a cardioversion/defibrillation shock, however, the intraventricular conduction system is left in a modified state which alters the subsequently generated electrogram signal. Use of the morphology criterion for SVT/VT discrimination is discontinued after delivery of such a shock and resumed after a predetermined minimum number of normally conducted ventricular beats has been detected.

22 Claims, 6 Drawing Sheets

OTHER PUBLICATIONS

"Non-Final Office Action Mailed Jul. 5, 2006 in U.S. Appl. No. 10/746,857", 14 pgs.

"Notice of Allowance mailed Nov. 1, 2007 in U.S. Appl. No. 10/746,857", 7 pgs.

"U.S. Appl. No. 10/746,857, Advisory Action mailed Aug. 3, 2007", 3 pgs.

"U.S. Appl. No. 10/746,857, Response filed Apr. 3, 2006 to Restriction Requirement mailed Mar. 3, 2006", 10 pgs.

"U.S. Appl. No. 10/746,857, Restriction Requirement mailed Mar. 3, 2006", 5 pgs.

"International Application Serial No. PCT/US2004/042196, International Search Report mailed Apr. 15, 2005", 4 pgs.

"International Application Serial No. PCT/US2004/042196, Written Opinion mailed Apr. 15, 2005", 7 pgs.

"Japanese Application Serial No. 2006-547137, Office Action mailed May 19, 2010", (w/ English Translation), 5 pgs.

"Japanese Application Serial No. 2006-547137, Office Action Response Filed:Nov. 26, 2010", 14 pgs.

"Japanese Application Serial No. 2006-547137, Notice of Allowance Feb. 10, 2011", 3 Pgs.

| V RATE LESS THAN OR EQUAL TO A RATE | MORPHOLOGY CORRELATED TO SINUS | ATRIAL RATE HIGH | UNSTABLE V RATE | DETECTED RHYTHM |
|---|---|---|---|---|
| N | X | X | X | VT |
| Y | N | N | N | VT |
| Y | N | N | Y | VT |
| Y | N | Y | N | VT |
| Y | X | Y | Y | SVT |
| Y | Y | X | X | SVT |

NOTE: X INDICATES THAT STATE OF DETECTION ENHANCEMENT DOES NOT AFFECT DETECTION OUTCOME.

Fig. 5

| MORPHOLOGY CORRELATED TO SINUS | UNSTABLE V RATE | DETECTED RHYTHM |
|---|---|---|
| N | N | VT |
| N | Y | SVT |
| Y | N | SVT |

Fig. 6

POST-SHOCK RECOVERY MONITORING FOR TACHYARRHYTHMIA DISCRIMINATION

CROSS REFERENCE TO RELATED APPLICATION

This application is a divisional of U.S. application Ser. No. 10/746,857, filed Dec. 24, 2003, now issued as U.S. Pat. No. 7,353,062, the specification of which is herein incorporated by reference.

FIELD OF THE INVENTION

This invention pertains to methods and apparatus for treating arrhythmias with electrical therapy and for discriminating between supraventricular and ventricular tachycardias.

BACKGROUND

Tachyarrhythmias are abnormal heart rhythms characterized by a rapid rate, typically expressed in units of beats per minute (bpm), which can originate in either the ventricles or the atria. Examples of tachyarrhythmias include atrial tachyarrhythmias such as atrial flutter and atrial fibrillation (AF), and ventricular tachyarrhythmias such as ventricular tachycardia (VT), and ventricular fibrillation (VF). In contrast, sinus tachycardia (ST) is a benign rhythm which can also result in an elevated heart rate with rates comparable to atrial and ventricular tachyarrhythmias in some patients. The most dangerous tachyarrhythmias are those that have their origin in the ventricles, namely ventricular tachycardia and ventricular fibrillation. Ventricular rhythms occur when re-entry of a depolarizing wavefront in areas of the ventricular myocardium with different conduction characteristics becomes self-sustaining or when an excitatory focus in the ventricle usurps control of the heart rate from the normal physiological pacemaker of the heart, the sino-atrial node. The result is rapid activation of the ventricles out of electromechanical synchrony with the atria. Most ventricular rhythms exhibit an abnormal QRS complex in an electrocardiogram (ECG) because they do not use the specialized conduction system of the ventricles, the depolarization spreading instead from the excitatory focus or point of re-entry directly into the myocardium. In ventricular tachycardia, the ventricles activate rapidly and produce distorted QRS complexes in an ECG. Ventricular fibrillation, on the other hand, occurs when the ventricles depolarize at an even more rapid rate and in a chaotic fashion, resulting in electrogram deflections of constantly changing shape and virtually no effective pumping action.

Implantable cardiac rhythm management devices may be configured to treat both atrial and ventricular tachyarrhythmias with electrical therapy. Devices known as implantable cardioverter/defibrillators (ICDs) deliver an electric shock to the heart which terminates the tachyarrhythmia by depolarizing all of the myocardium simultaneously and rendering it refractory. The most dangerous tachyarrhythmias are ventricular tachycardia and ventricular fibrillation, and ICDs have most commonly been applied in the treatment of those conditions. Both ventricular tachycardia and ventricular fibrillation can be hemodynamically compromising, and both can be life-threatening. Ventricular fibrillation, however, causes circulatory arrest within seconds and is the most common cause of sudden cardiac death and is usually treated with immediate delivery of a defibrillation shock. Ventricular tachycardia can be treated with either a defibrillation or a cardioversion shock, the latter referring to a shock delivered synchronously with an R wave. Dual chamber ICDs are also capable of detecting atrial tachyarrhythmias, such as atrial fibrillation and atrial flutter, and delivering a cardioversion shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, dual chamber ICDs configured to treat atrial fibrillation offer a number of advantages to certain patients, including convenience and greater efficacy.

Another type of electrical therapy for ventricular tachycardia is anti-tachycardia pacing (ATP). In ATP, the ventricles are competitively paced with one or more pacing pulses in an effort to interrupt the reentrant circuit causing the tachycardia. ATP therapy can successfully treat VT, but it is not effective in terminating VF. Modern ICDs incorporate ATP capability so that ATP therapy can be delivered to the heart when a ventricular tachycardia is detected. Although cardioversion/defibrillation will also terminate ventricular tachycardia, it consumes a large amount of stored power from the battery and results in patient discomfort owing to the high voltage of the shock pulses. It is desirable, therefore, for the ICD to use ATP to terminate a tachyarrhythmia whenever possible. In most ICDs with ATP capability, VF is distinguished from VT using a rate-based criterion so that ATP or shock therapy can be delivered as appropriate, where the heart rate is determined by measurement of the time interval between successive ventricular depolarizations. In a typical device, therapy delivery may be programmably allocated into multiple rate zones, with VF therapy delivered in the highest zone, and VT therapy delivered in one or more lower rate zones. A tachyarrhythmia with a heart rate in the VT zone may be treated with ATP therapy in order to avoid an unnecessary painful shock to the patient, and a defibrillation shock is delivered if the heart rate is in the VF zone or if ATP pacing fails to terminate a tachyarrhythmia in the VT zone.

As aforesaid, VT can be detected when the ventricular rate falls within the VT zone. A rapid ventricular rate in the VT zone, however, is not necessarily due to VT but can also result from a tachycardia that originates from "above" the ventricles. Such tachyarrhythmias are referred to as supraventricular tachycardias (SVT's) and include ST, which is a normal rhythm, as well as atrial tachyarrhythmias such as atrial tachycardia (AT) of non-sinus origin, atrial flutter (AFL), AV node reentrant tachycardia (AVNRT), and atrial fibrillation (AF). The normal rhythmic impulse of the heart is first generated in pacemaker tissue known as the sino-atrial (SA) node, spreads throughout the atria causing atrial contraction, and is then conducted to the atrioventricular (AV) node where the impulse is delayed before passing into the ventricles. The ventricles of a normal heart are then electrically stimulated by excitation emanating from the AV node that spreads via specialized conduction pathways. An abnormal rhythm in the atria can thus be transmitted antegradely to the ventricles in a patient whose AV conduction pathway is intact. Such an SVT is characterized by elevated rates in both the atria and the ventricles. Elevated rates in both the atria and ventricles can also occur with VT as well, however, due to retrograde conduction of excitation from the ventricles to the atria. Such retrograde conduction is possible in most people and confounds the discrimination between VT and SVT based upon atrial and ventricular rates alone when both rates are similar, a condition known as a one-to-one or 1:1 tachycardia.

It is desirable for an ICD to differentiate between an SVT and a VT, to ensure delivery of appropriate therapy. Ventricular ATP therapy delivered to treat an SVT will not be effective and potentially could make matters worse by triggering a ventricular arrhythmia. Ventricular shock therapy delivered into SVTs can be perceived as painful and is ineffective in reducing elevated heart rates associated with ST. It is thus important for an ICD to recognize that an elevated ventricular rate is due to an SVT rather than a VT so that ventricular ATP therapy can be withheld and specific therapy for the atrial tachyarrhythmia can be delivered if appropriate. Conversely, because VT is generally a more serious condition, the ICD also needs to detect VT with a high degree of sensitivity so that therapy can be delivered promptly. The present invention is directed toward improvements in methods and apparatus for dealing with this problem.

SUMMARY

A primary technique for distinguishing supraventricular tachyarrhythmias from VT (referred to as SVT/VT discrimination) is by a rate based test involving measured atrial and/or ventricular rates. For example, a rate based test may judge a tachyarrhythmia as a VT if the ventricular rate is greater than a specified VT threshold and also greater than the atrial rate. Additional rate based criteria such as suddenness of onset of the fast ventricular rate, stability of the ventricular rate, and presence of a high atrial rate above a predetermined or programmable threshold may also be applied to distinguish VT from SVT and atrial tachyarrhythmias from ST. Discrimination between VT and SVT can be aided by additionally employing a morphology criterion in which the morphology of electrogram waveforms during ventricular beats are analyzed to determine if the beats are normally conducted. A combined morphology/rate based test can then be used for discriminating between SVT and VT. An exemplary morphology/rate based algorithm judges a tachyarrhythmia in which the ventricular rate is above a specified VT threshold as an SVT only if: 1) the atrial rate is greater than or equal to the ventricular rate, and 2) some predetermined minimum number of ventricular beats has been detected as normally conducted according to the morphology criterion, or another indication of SVT is present such as an unstable ventricular rate in combination with a high atrial rate.

An implantable cardiac rhythm management device may treat VF and AF by the delivery of ventricular defibrillation shocks or atrial conversion shocks. After the delivery of such a shock, however, conduction within the heart is left in a modified state which alters a subsequently generated electrogram signal so that use of the morphology/rate test must be temporarily discontinued until the conduction system recovers. A post-shock recovery period may therefore be defined during which only a rate based test, rather than the combined morphology/rate test, is used for SVT/VT discrimination. A fixed post-shock recovery period can be used so that the combined morphology/rate test is discontinued for a predetermined period of time following each shock. It is desirable, however, to resume use of the combined morphology/rate test as soon as possible in order to permit more sensitive detection of atrial tachyarrhythmias and consequent delivery of appropriate therapy. This is especially important in the case of atrial cardioversion shocks delivered to terminate atrial fibrillation since early recurrence of atrial fibrillation (ERAF) is not an uncommon event. In accordance with the present invention, therefore, use of the morphology/rate test to distinguish between an SVT and a VT is resumed after a predetermined minimum number of normally conducted ventricular beats has been detected as determined by the same or a different morphology criterion used in the morphology/rate test for SVT/VT discrimination.

DETAILED DESCRIPTION

As noted above, ICDs may be configured for delivering ventricular anti-tachycardia pacing or shocks in order to terminate ventricular tachycardias and for delivering atrial anti-tachycardia pacing or atrial conversion shocks in order to terminate atrial tachyarrhythmias, and it is important for such devices be able to distinguish between an SVT and VT. One way by which a device may distinguish between an SVT and VT is to employ a rate based test so that if a ventricular rate is detected that is high enough to constitute a VT, the arrhythmia is categorically classified as a VT if the ventricular rate is also greater than the atrial rate. A tachycardia in which the atrial rate is greater than or equal to the ventricular rate, on the other hand, may be a VT, an SVT, or a dual tachycardia where both VT and SVT are present simultaneously. Since VT is the more serious condition and requires prompt treatment, the rate based test may require that one or more additional rate based criteria be met before VT is ruled out. Such criteria, which help identify SVT, may include instability of the ventricular rate and an atrial rate above a specified atrial tachyarrhythmia threshold. Only if these one or more additional criteria are met is the tachycardia then classified as an SVT. The atrial tachyarrhythmia threshold may also be used to further classify the SVT as an atrial tachyarrhythmia requiring treatment, such as atrial fibrillation, or as ST which is not considered an arrhythmia and requires no treatment.

In order to more accurately detect an SVT, a combined morphology/rate based test may be used instead of the rate based test described above for SVT/VT discrimination. In a combined morphology/rate based test, a morphology criterion based upon a morphology analysis of electrogram waveforms is used to provide an additional criterion for detecting an SVT. For example, SVT may be detected if: 1) the atrial rate is greater than or equal to the ventricular rate and, 2) some minimum number of ventricular beats are judged as normally conducted as determined by a morphology criterion involving morphology analyses of electrogram waveforms. An exemplary implementation of a morphology criterion for SVT/VT discrimination is disclosed in U.S. Pat. No. 6,449,503, assigned to Cardiac Pacemakers, Inc., the disclosure of which is hereby incorporated by reference in its entirety.

A morphology analysis may be performed for purposes of implementing a morphology criterion in different ways, such as by identifying particular features in the an electrogram signal generated during a particular ventricular beat and by comparing an electrogram signal generated during a particular ventricular beat with a reference template representing a normally conducted ventricular beat. One means by which an electrogram signal may be compared with a template is by performing a cross-correlation between the electrogram signal and the template. If the beat electrogram signal and the reference template are sufficiently correlated, the ventricular beat can then be judged as normally conducted. The comparison of the beat electrogram waveform and the reference template waveform may be performed by computing a feature correlation coefficient between selected corresponding features of the two waveforms where the selected features may represent amplitudes of the electrogram waveform at various points. An exemplary formula for computing a feature correlation coefficient (FCC) is given by:

$$FCC = (N\Sigma X_i Y_i - (\Sigma X_i)(\rho Y_i))^2 / (N\rho X_i^2 - (\rho X_i)^2)(N\rho Y_i^2 - (\rho Y_i)^2)$$

where $X_i$ represent beat features, $Y_i$ represent template features, N is the number of features, and the summations are carried out from i to N. In a particular embodiment of a morphology criterion, N is equal to 8, and a ventricular beat is judged as normally conducted if FCC is greater than 0.94. In order for the beat morphology to be correlated to the template as opposed to inversely correlated with an inverted morphology, the following additional condition must be met:

$$N\rho X_i Y_i - (\rho X_i)(\rho Y_i) > 0$$

Morphology discrimination is possible from the ventricular pacing electrodes. However, the beat electrogram signal for morphology analysis is preferably obtained from electrodes which record a signal that captures overall ventricular dynamics. Such electrodes may be described as having a "unipolar" configuration in that several centimeters separate the electrodes. "Unipolar" electrodes positioned so that a large portion of the heart falls between them "see" a larger volume of the myocardium, and changes in the depolarization pattern of the ventricles will be more readily reflected in an electrogram generated by the electrode during a ventricular beat. A convenient electrode for this purpose is the shock electrode that the device normally uses for delivering cardioversion/defibrillation shocks. The sensing channel incorporating the shock electrode and which is used to generate electrograms for morphology analysis is referred to herein as the shock channel. It should be appreciated that a sensing channel for generating electrograms suitable for morphology analysis could use an electrode other than the shock electrode. In the description that follows, the term shock channel should be taken to mean any sensing channel used to generate electrograms for morphology analysis, regardless as to whether a shock electrode is actually used.

In order to ensure that corresponding features of the beat and template waveforms are used in computing the feature correlation coefficient, the two waveforms must be aligned with respect to some temporal reference point. Such alignment may be accomplished by recording a bipolar electrogram using a sensing channel normally used to sense R waves for rate determination, referred to as the rate channel, simultaneously with the shock channel electrogram used as the beat electrogram. The reference template electrogram is then aligned with respect to a selected alignment point of the rate channel electrogram (the peak amplitude of the QRS complex). Amplitudes of the shock channel electrogram and the reference template occurring at predetermined times with respect to the alignment point are then used as the features for computing the feature correlation coefficient.

Immediately following delivery of a cardioversion/defibrillation shock, however, morphology analysis of electrogram waveforms is no longer able to reliably identify normally conducted beats. The reason for this is that, after a shock pulse is output from electrodes, the electrical conduction within the heart is temporarily modified, so that conduction of supraventricular beats proceeds through the ventricular myocardium with a different vector until conduction recovers, resulting in a depolarization waveform with altered morphology and which may have inverted polarity. Use of the combined morphology/rate test for SVT/VT discrimination should therefore be discontinued after a cardioversion/defibrillation shock is delivered until the conduction system recovers. Following delivery of an atrial conversion or ventricular defibrillation/cardioversion shock, the device could initiate a fixed post-shock recovery period, during which only a rate based test is used for SVT/VT discrimination so that a ventricular rate in the VT zone which is greater than or equal to the atrial rate is detected as a VT. It is desirable to resume use of the morphology/rate based test as soon as possible, however, because all 1:1 tachycardias and some other SVT's will be interpreted by the rate based test as VT. This increases the probability that inappropriate therapy (i.e., ventricular anti-tachycardia pacing or shock) will be delivered to treat an SVT. This situation is particularly likely to occur following delivery of an atrial conversion shock to treat AF due to the phenomenon of early recurrence of atrial fibrillation or ERAF. ERAF is defined as the recurrence of atrial fibrillation within a few minutes after successful cardioversion with atrial shock therapy, and certain patients are more prone to experience it than others.

In accordance with the present invention, a cardiac rhythm management device is configured to generate an electrogram signal from a cardiac sensing channel and programmed to utilize a morphology criterion derived from analysis of the electrogram signal for SVT/VT discrimination. The device is further programmed to discontinue use of the morphology criterion for SVT/VT discrimination after delivery of a cardioversion/defibrillation shock and to resume use of the morphology criterion for SVT/VT discrimination when a predetermined minimum number of ventricular beats has been judged as normally conducted. Ventricular beats may be judged as normally conducted through the use of rate measurements, morphology analysis, or both.

In an exemplary embodiment, a dual-chamber or single-chamber defibrillator is configured to discontinue use of a morphology criterion in a combined morphology/rate based test for SVT/VT discrimination immediately following delivery of a cardioversion/defibrillation shock. In order to minimize the time period following the shock during which the morphology criterion is not used for SVT/VT discrimination, the device is further configured to monitor the electrogram signals generated by the shock channel during the normal sinus rhythm following successful termination of the atrial or ventricular tachyarrhythmia. Each shock channel electrogram can then be judged as normally conducted or not using the same or a different morphology criterion used by the morphology/rate based test in distinguishing between an SVT and a VT. When normal sinus rhythm is present (as determined by measurement of the atrial and/or ventricular rates), all of the ventricular beats can be assumed to be normally conducted (i.e., supraventricular rhythm is present). Therefore, detection of a normally conducted beat from the shock channel electrogram during the post-shock period implies that the intra-ventricular conduction system has recovered to its normal state and that electrograms will exhibit normal depolarization morphology. In accordance with the invention, the device is configured to resume use of the morphology criterion as part of a combined morphology/rate based test to distinguish between an SVT and a VT after a predetermined minimum number of normally conducted ventricular beats has been detected. A particular embodiment of the invention is described in more detail below.

1. Exemplary Device Description

Figure 1:
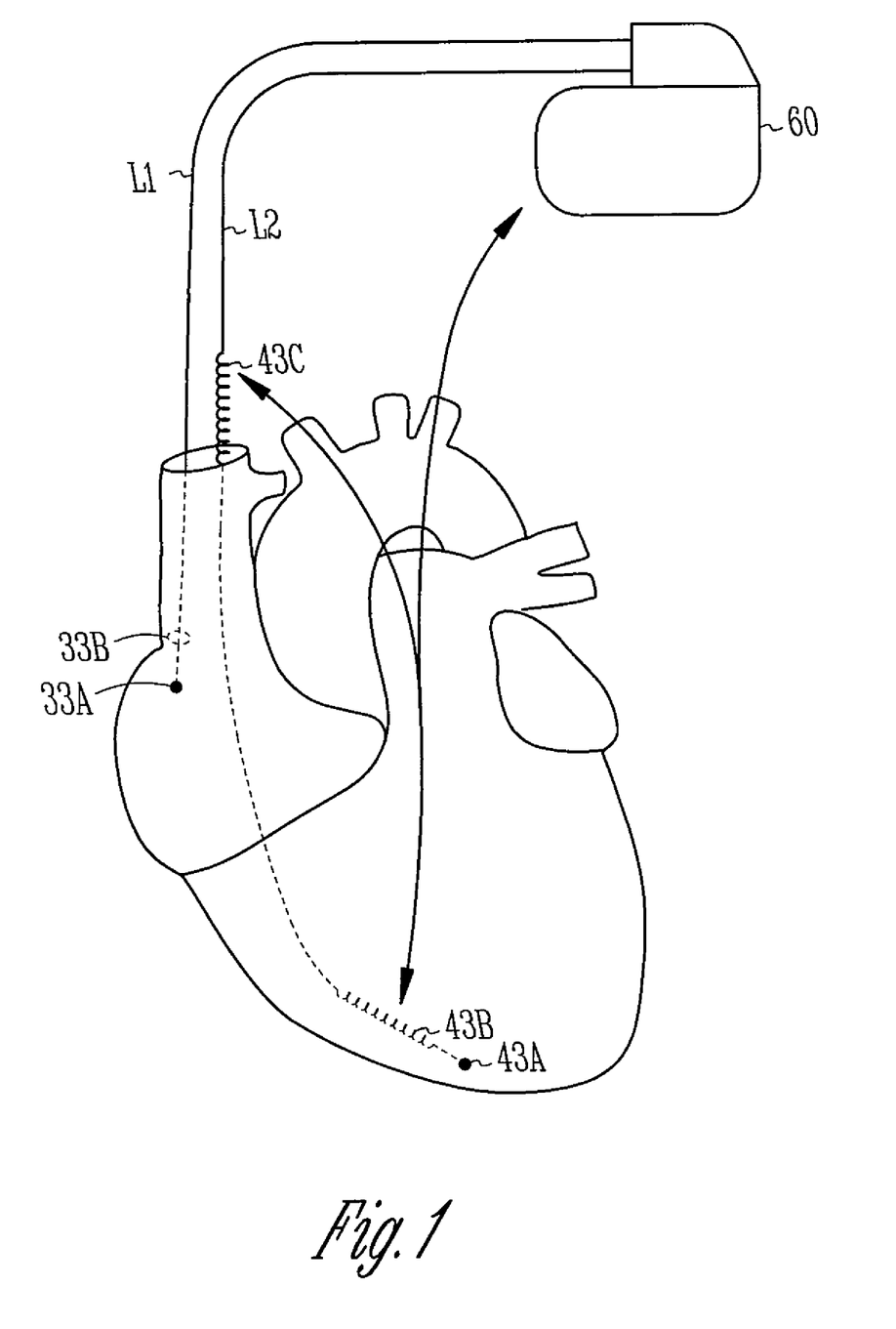
FIG. 1 depicts an exemplary physical configuration of an implanted cardiac rhythm management device.

Cardiac rhythm management devices such as ICDs and pacemakers are typically implanted subcutaneously on a patient's chest and have leads threaded intravenously into the heart to connect the device to electrodes used for sensing cardiac activity, delivering pacing pulses, and/or delivering defibrillation shocks. FIG. 1 depicts an implantable cardioverter/defibrillator device for treating atrial and ventricular tachyarrhythmias that also incorporates functionality for pacing the atria and/or the ventricles. The device includes a subcutaneously implantable housing or can 60 for enclosing the electronic circuitry of the device and a pair of leads L1 and L2 having electrodes incorporated therein. The lead L1 has a tip electrode 33a and ring electrode 33b which are shown in the figure as disposed in the right atrium (RA) for pacing or sensing of the atria. The lead L2 has a tip electrode 43a, a distal coil electrode 43b, and a proximal coil electrode 43c. In the placement of the lead L2 shown in the figure, tip electrode 43a and distal coil electrode 43b are disposed in the right ventricle (RV), and proximal coil electrode 43c is disposed in the superior vena cava or right atrium. Sensing or pacing of the ventricles may be performed, e.g. using tip electrode 43a as the cathode and coil electrode 43b as the anode. A ventricular cardioversion/defibrillation shock or an atrial conversion shock may be delivered between coil 43b and the can 60, between the coil 43b and coil 43c, or between coil 43b and the can 60 electrically in common with the coil 43c.

Figure 2:
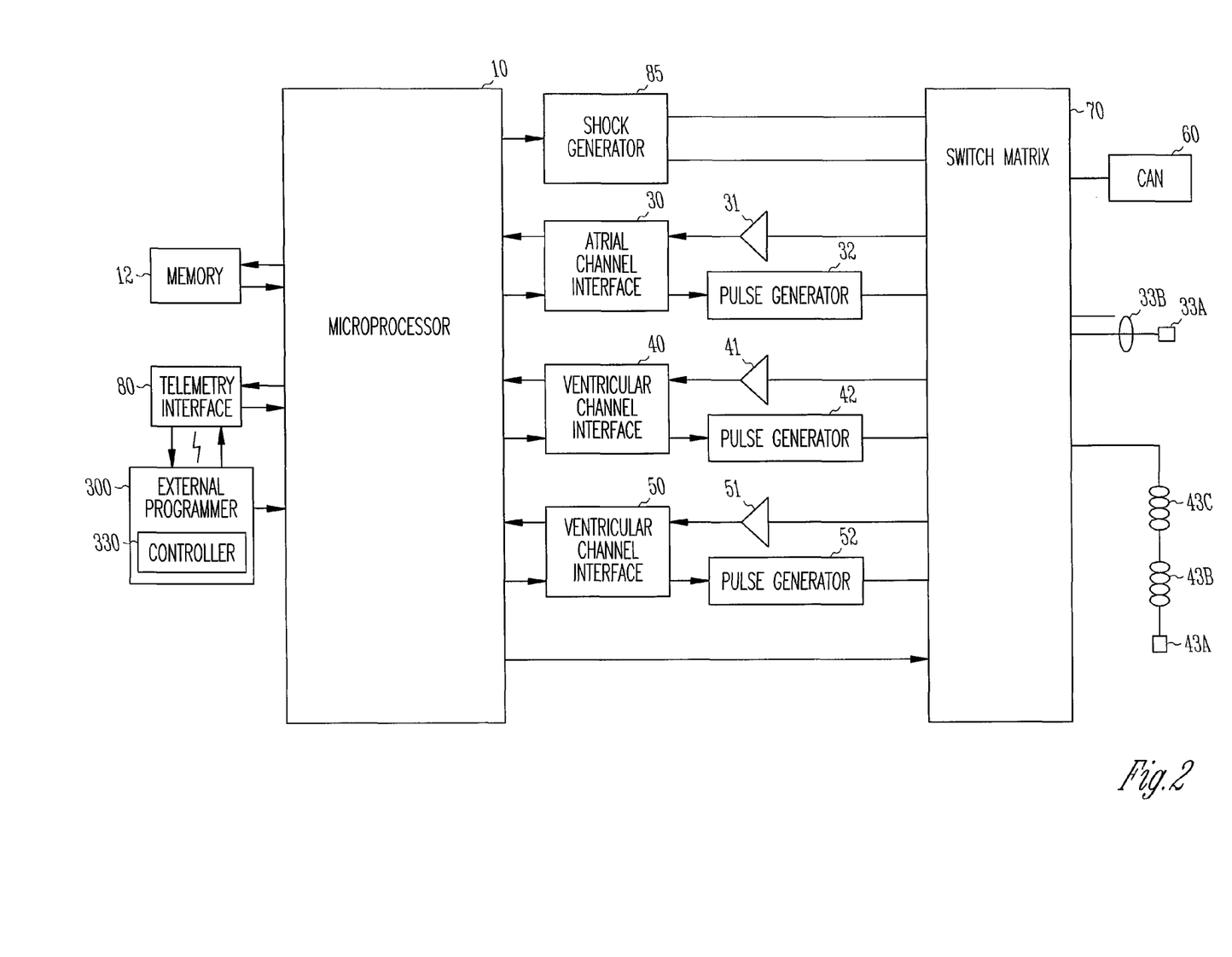
FIG. 2 is a system diagram of an implantable cardiac rhythm management device.

FIG. 2 is a system diagram of the implantable device shown in FIG. 1. The controller of the device is made up of a microprocessor 10 communicating with a memory 12, where the memory 12 may comprise a ROM (read-only memory) for program storage and a RAM (random-access memory) for data storage and additional program storage. A microprocessor-type controller 10 controls the overall operation of the device in accordance with programmed instructions stored in memory. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor. A telemetry interface 80 is provided for communicating with an external programmer 300. The external programmer is a computerized device with a controller 330 that can interrogate the device and receive stored data as well as adjust the device's operating parameters. The device is equipped with multiple sensing amplifiers and pulse generators which can be configured as channels for pacing and/or sensing selected heart chambers. A switch matrix 70 controlled by the microprocessor is used to configure a sensing or pacing channel by switching selected electrodes to the input of a sense amplifier or to the output of a pulse generator. The switch matrix 70 allows the device to employ either bipolar sensing/pacing using two closely spaced electrodes of a lead or unipolar sensing/pacing using one of the electrodes of a lead and the can 60 as a reference electrode. The switch matrix 70 can connect shock generator 85 to deliver a ventricular cardioversion/defibrillation shock or atrial conversion shock between coil electrode 43b and the can 60 (or the coil electrode 43c, or the can 60 connected in common with the coil electrode 43c). In the device shown in FIG. 2, an atrial channel for sensing or pacing an atrial site is configured with tip electrode 33a, ring electrode 33b, sense amplifier 31, pulse generator 32, and an atrial channel interface 30 which communicates bidirectionally with a port of microprocessor 10. A first ventricular channel for sensing or pacing a ventricular site is configured with tip electrode 43a, coil electrode 43b, sense amplifier 41, pulse generator 42, and ventricular channel interface 40. This channel may be used as the rate channel referred to earlier which generates an electrogram for aligning the reference template waveform. A second ventricular sensing channel using ventricular channel interface 50 may be configured by connecting one of the differential inputs of sense amplifier 51 to the coil electrode 43b and connecting the other input to the can 60 and coil electrode 43c. This is the shock channel for generating the beat electrogram used for morphology analysis as described above.

The channel interfaces may include comparators for comparing received electrogram signals to reference values, analog-to-digital converters for digitizing sensing signal inputs from the sensing amplifiers, registers that can be written to for adjusting the gain and sensing threshold values of the sensing amplifiers, and registers for controlling the output of pacing pulses and/or adjusting the pacing pulse energy by changing the pulse amplitude or pulse width. The controller uses the sensing channels in order to detect intrinsic cardiac activity in a heart chamber, referred to as a chamber sense (e.g., an atrial sense or a ventricular sense). In order to detect intrinsic cardiac activity, the signals emanating from the sense amplifier are compared with a reference potential. As described above, a sensing channel includes sense amplifier circuits for amplifying and filtering the electrogram signals picked up by an electrode disposed at a cardiac site. Only when an electrogram signal from the sense amplifier exceeds a reference potential, referred to as a sensing threshold, is it treated as a chamber sense. The sensing threshold may be implemented with analog circuitry, where the sense amplifier output is applied to one input of a comparator circuit whose other input is connected to a reference potential, or with digital circuitry operating on digitized samples of the sense amplifier output which are compared with a digitized reference value. In either case, the sensing threshold for each channel is adjustable by the controller. Detected chamber senses may be used for controlling the delivery of paces in accordance with a programmed pacing mode (e.g., ventricular anti-tachycardia pacing) and/or for diagnostic purposes. By counting the number of chamber senses over a defined time period, the controller is able to measure heart rate and detect arrhythmias using rate-based criteria. The atrial sensing channel and the first ventricular sensing channel described above are used to separately measure the atrial and ventricular rates in this embodiment.

When the measured atrial and/or ventricular rates exceed specified threshold values, the device detects an arrhythmia and is programmed to respond with appropriate therapy. For example, if a ventricular rate is measured which is in the VF zone, the device delivers a ventricular defibrillation shock. If a ventricular rate is measured which is in the VT zone, the device decides whether VT or an SVT is present using the rate and morphology criteria described above. If the ventricular rate is greater than the atrial rate, VT is detected, and the device may be programmed to initiate ventricular anti-tachycardia pacing or a ventricular shock. If the atrial rate is greater than or equal to the ventricular rate and a specified minimum number of normally conducted beats are detected, an SVT is detected, and, if the SVT is classified as an atrial tachyarrhythmia, the device may be programmed to deliver atrial anti-tachycardia pacing or an atrial cardioversion shock. Rate stability, suddenness of onset, and/or atrial rate criteria can also be used as additional criteria to classify the arrhythmia as atrial in origin when the ventricular rate is in the VT zone. A dual chamber defibrillator, such as illustrated by FIG. 2, would also detect an atrial tachyarrhythmia and deliver an atrial anti-tachycardia pacing or an atrial cardioversion shock if the atrial rate is above a specified threshold value and the ventricular rate is in the normal range, as could occur in a patient without an intact AV conduction pathway. To lessen the risk of inducing a ventricular arrhythmia, the device may deliver the atrial cardioversion shock synchronously with a sensed ventricular depolarization (i.e., an R wave) and may delay delivering the shock until the interval from the previous ventricular beat meets certain criteria, e.g. is longer than a predetermined or programmable threshold. Methods for R-wave synchronization are described in U.S. Pat. No. 5,207,219, hereby incorporated by reference.

The device illustrated in FIG. 2 is a dual-chamber defibrillator having the capability of sensing both the atria and the ventricles and of delivering shock and/or ATP therapy to both the atria and the ventricles. Various embodiments of the invention may be incorporated into devices possessing either some or all of the components illustrated in FIG. 2. For example, the post-shock recovery monitoring algorithms in accordance with the invention may be incorporated into a dual-chamber defibrillator having atrial and ventricular sensing capability, a single-chamber defibrillator having atrial and ventricular sensing capability, or a single-chamber defibrillator having only ventricular sensing capability.

2. Exemplary Post-Shock Recovery Monitoring Algorithms

In an exemplary embodiment of the invention, a cardiac rhythm management device such as depicted in FIG. 2 is configured to distinguish between VT and SVT by using a combined morphology/rate test as described above. To perform the morphology analysis, the beat electrogram is correlated with a template to determine if a beat is normally conducted. The beat electrogram is obtained from a shock channel incorporating the shock electrode used to deliver cardioversion and/or defibrillation shocks. The device distinguishes between SVT and VT with a combined morphology/rate based test which includes: a) a rate criterion involving the measured atrial and ventricular rates, and b) a morphology criterion, wherein a first predetermined minimum number of beats must be judged as normally conducted ventricular beats before an SVT is detected. After detecting a tachyarrhythmia and subsequently restoring normal sinus rhythm with an atrial cardioversion or ventricular cardioversion/defibrillation shock delivered through the shock electrode, the device discontinues use of the combined morphology/rate based test to distinguish between an SVT and a VT and employs a rate based test instead. The use of the combined morphology/rate based test is then resumed only when a second predetermined minimum number ventricular beats during supraventricular rhythm has been judged as normally conducted.

Figure 5:
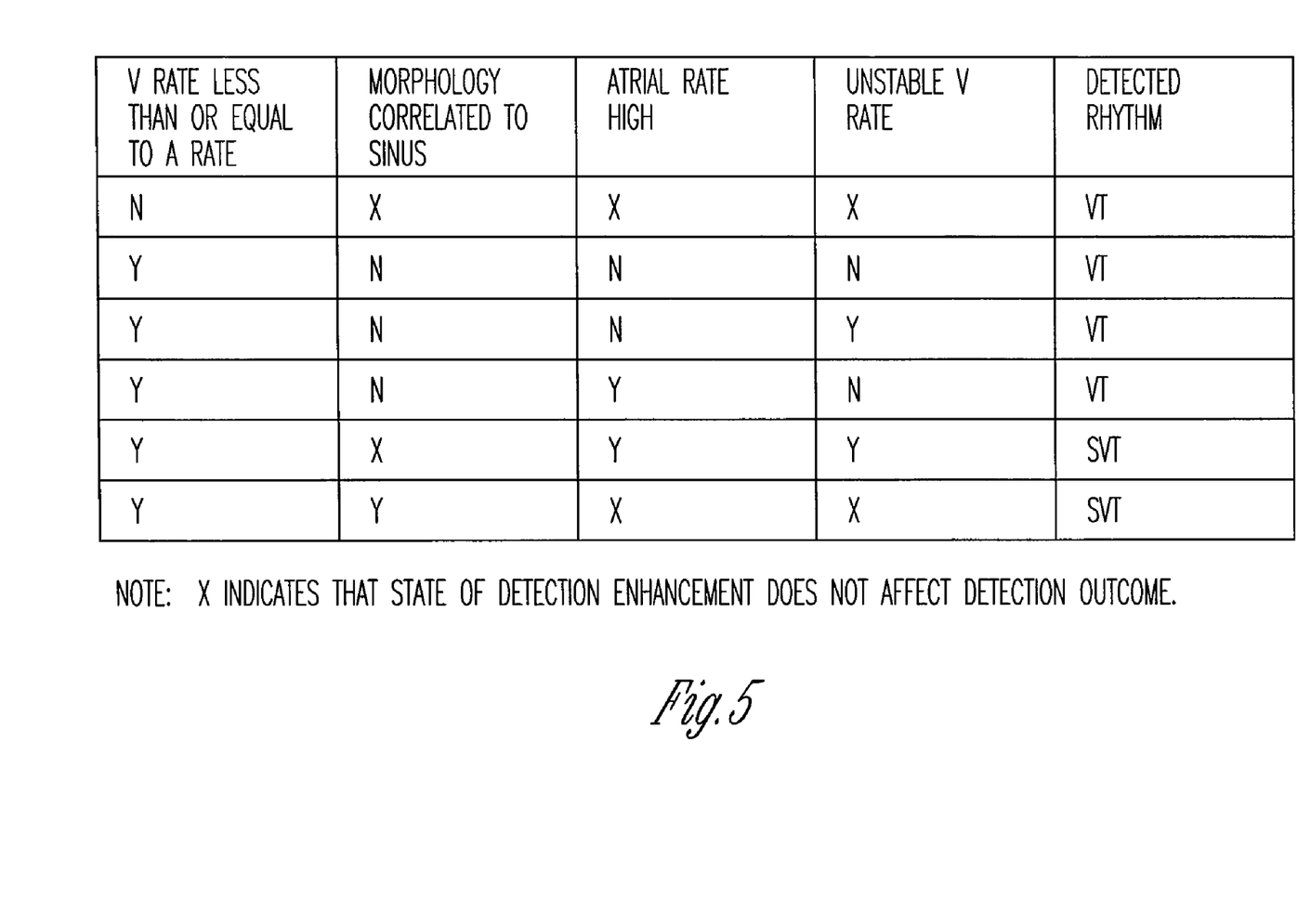
FIG. 5 illustrates a truth table of an exemplary method for combining morphology and rate based criteria yielding an overall SVT/VT discrimination decision for dual chamber defibrillators and ventricular defibrillators with dual chamber sensing and pacing.

FIG. 5 is a truth table representation of a combined rate/morphology based test for SVT/VT discrimination utilizing measurements of both the atrial and ventricular rates. Such a test could be implemented by a dual chamber defibrillator or a ventricular defibrillator with both atrial and ventricular sensing capability.

Figure 3:
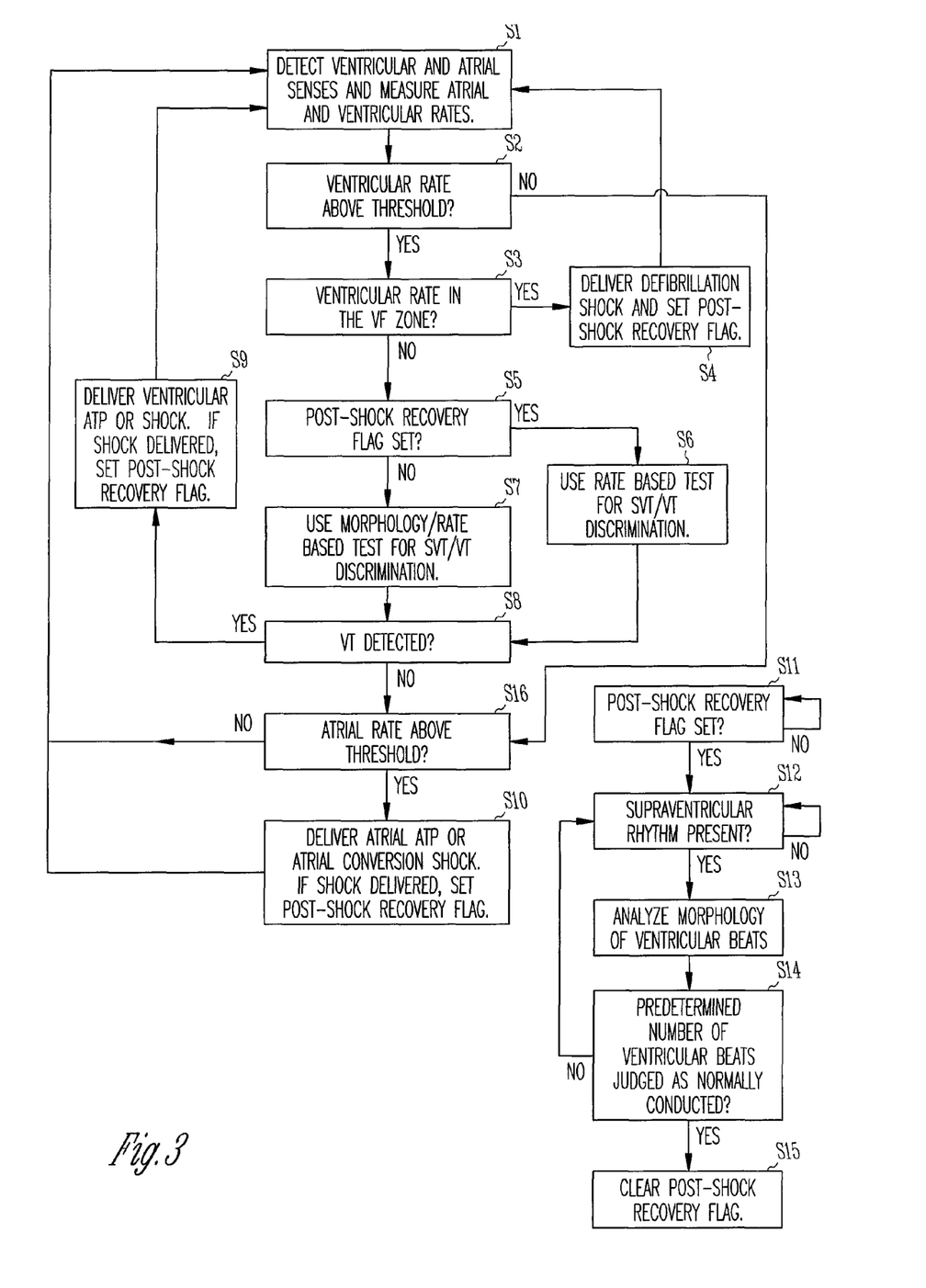
FIG. 3 illustrates an exemplary algorithm for post-shock recovery monitoring and resuming use of a morphology criterion for tachyarrhythmia discrimination following delivery of an atrial or ventricular cardioversion shock for a dual chamber defibrillator.

FIG. 3 illustrates an exemplary algorithm, as would be implemented by appropriate programming of the controller, by which a dual chamber defibrillator utilizing both a rate based test and a combined morphology/rate based test for SVT/VT discrimination may perform post-shock recovery monitoring in order to determine when a valid electrogram for morphology analysis can be used after a shock is delivered. In this embodiment, both a rate based test and a combined morphology/rate based test are used for SVT/VT discrimination. In an exemplary rate based test, a tachycardia is classified as an SVT if the atrial rate is greater than a preset threshold (e.g., 200 bpm), the atrial rate is greater than or equal to the ventricular rate, and the ventricular rate is unstable. Instability of the ventricular rate may be determined by measuring the differences between successive RR intervals (i.e., intervals between ventricular senses), computing an average of those differences, comparing the average to a preset threshold (e.g., 20 ms), and deeming the ventricular rate to be unstable if the average exceeds the threshold. In an alternate embodiment of the rate based test, the test may also judge a tachycardia as a VT if the ventricular rate is greater than the atrial rate or the ventricular rate is suddenly increased and stable. This is useful in distinguishing VT which usually starts with a sudden increase in rate from sinus tachycardia which usually begins with a gradual increase in rate. In an exemplary combined morphology/rate based test utilizing measurements of both atrial and ventricular rates, as illustrated by FIG. 5 in the form of a truth table, a tachyarrhythmia is judged as an SVT if: 1) the measured atrial rate is greater than or equal to the measured ventricular rate and 2) a predetermined minimum fraction of a specified number of ventricular beats has been judged as normally conducted or the combined conditions of high atrial rate (e.g. >200 bpm) and ventricular rate instability are present.

Referring to FIG. 3, atrial and ventricular rates are measured from sensed atrial and ventricular electrical activity at step S1 in order to detect atrial and ventricular tachyarrhythmias. If no ventricular arrhythmia is detected at step S2, the presence of an atrial tachyarrhythmia is checked at step S16 as discussed below. If a ventricular arrhythmia is detected at step S2 because the ventricular rate is above a specified threshold, the device next determines what type of arrhythmia is occurring in order to deliver appropriate therapy. If the arrhythmia is in the VF zone as determined at step S3, a defibrillation shock is delivered and a post-shock recovery flag is set at step S4. Otherwise, the arrhythmia may either be VT or SVT such as atrial fibrillation. At step S5, it is determined whether the post-shock recovery flag is set or cleared. If the flag is set, only a rate based test is used for SVT/VT discrimination at step S6. If, on the other hand, the post-shock recovery flag is cleared, the algorithm employs a combined morphology/rate based test for SVT/VT discrimination at step S7. An electrogram signal is generated from the shock electrode, and a feature correlation coefficient is computed for selected ventricular beats. The feature correlation coefficient reflects the extent of correlation between a reference template representing normal ventricular conduction and the electrogram signal generated from the shock electrode, and a ventricular beat is judged as normally conducted if the feature correlation coefficient exceeds a predetermined threshold value (e.g., 94%). An SVT and a VT are distinguished according to the combined morphology/rate based test which detects an arrhythmia as an SVT if: 1) the measured atrial rate is greater than or equal to the measured ventricular rate and some predetermined minimum fraction of a specified number of ventricular beats has been judged as normally conducted, or 2) if the atrial rate is greater than a preset threshold, the atrial rate is greater than or equal to the ventricular rate, and the ventricular rate is unstable. If a ventricular tachycardia is detected by either the rate based test or the morphology/rate based test at step S8, VT therapy is delivered at step S9, and the algorithm returns to step S1. If no VT is detected at step S8, the atrial rate is evaluated at step S16 to determine if an atrial tachyarrhythmia is present. (In the case of a device with no atrial therapy capability, the algorithm would return to step S1 if no VT is detected at step S8.) If an atrial tachyarrhythmia is not detected at step S16, then the algorithm returns to step S1. If an atrial tachyarrhythmia is detected, an atrial therapy is delivered at step S10. If a shock is delivered at steps S9 or S10, then the post-shock recovery flag is set. The algorithm then returns to step S1 and, concurrently, a post-shock recovery monitoring routine begins at step S11. At step S12, the device determines if supraventricular rhythm exists. When supraventricular rhythm is present, the device proceeds to step S13 where the morphology of one or more beat electrograms are analyzed using the same or different morphology criterion used in distinguishing between an atrial tachyarrhythmia and a ventricular tachycardia. After a predetermined minimum number of normally conducted ventricular beats has been detected at step S14, the post-shock recovery flag is cleared at step S15.

Figure 4:
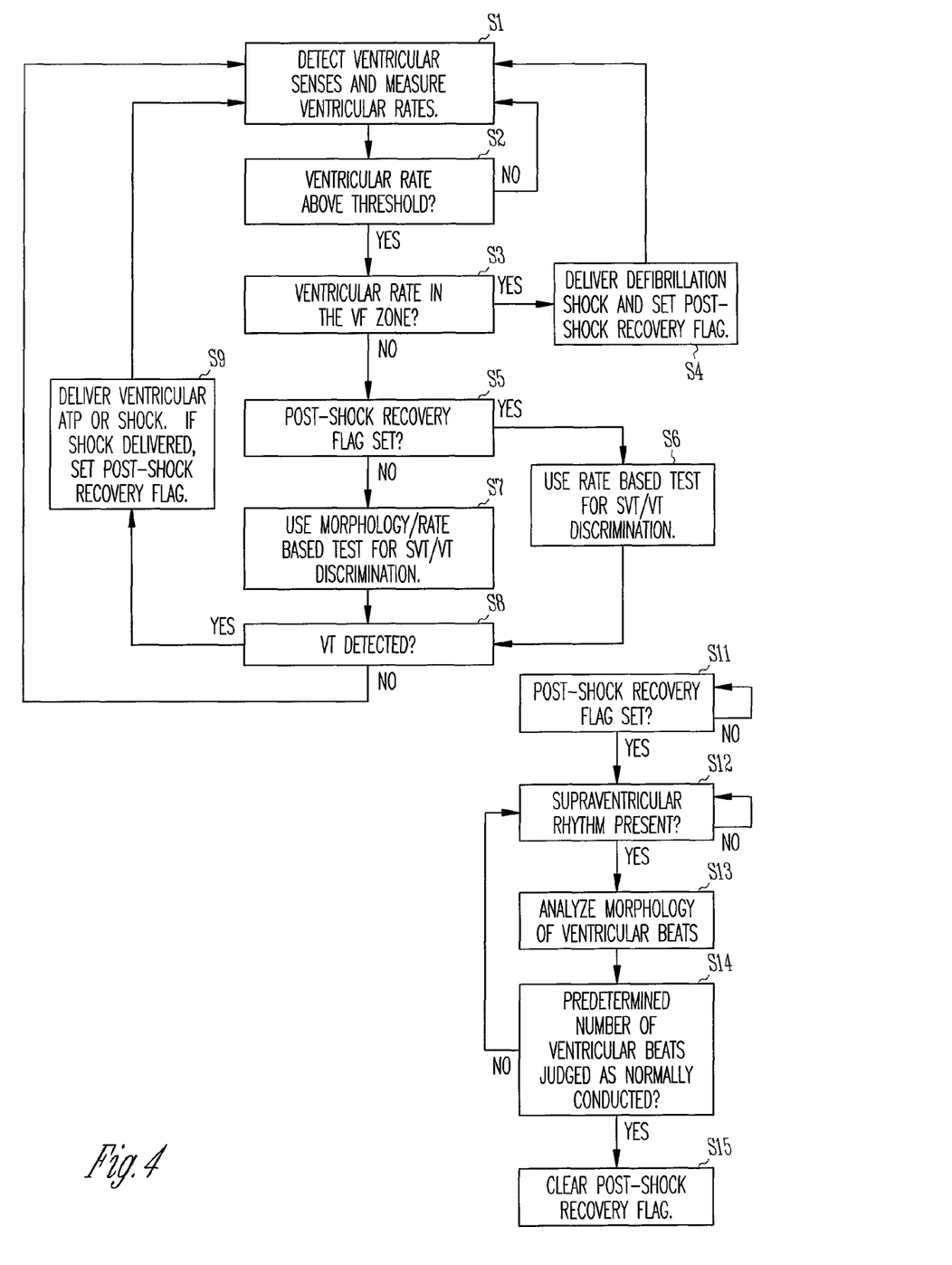
FIG. 4 illustrates an exemplary algorithm for post-shock recovery monitoring and resuming use of a morphology criterion for tachyarrhythmia discrimination following delivery of a ventricular cardioversion shock for a ventricular defibrillator.

FIG. 4 illustrates an exemplary algorithm for a single chamber defibrillator, as would be implemented by appropriate programming of the controller, by which the device may perform post-shock recovery monitoring in order to determine when a valid electrogram for morphology analysis can be used after a shock is delivered. This algorithm is similar to that of the dual chamber defibrillator illustrated by FIG. 3, but does not provide atrial defibrillation shock or atrial ATP and utilizes ventricular sensing only. Thus, only the ventricular rate is measured at S1, and steps S10 and S16 of FIG. 3 are omitted in FIG. 4. As in the above-described dual chamber embodiment, both a rate based test and a combined morphology/rate based test are used for SVT/VT discrimination. These tests may be similar to those previously described for the dual chamber defibrillator algorithm except that no measurements of the atrial rate are used. For example, the rate based test may judge a tachycardia as a VT rather than an SVT if the ventricular rate is suddenly increased and stable.

Figure 6:
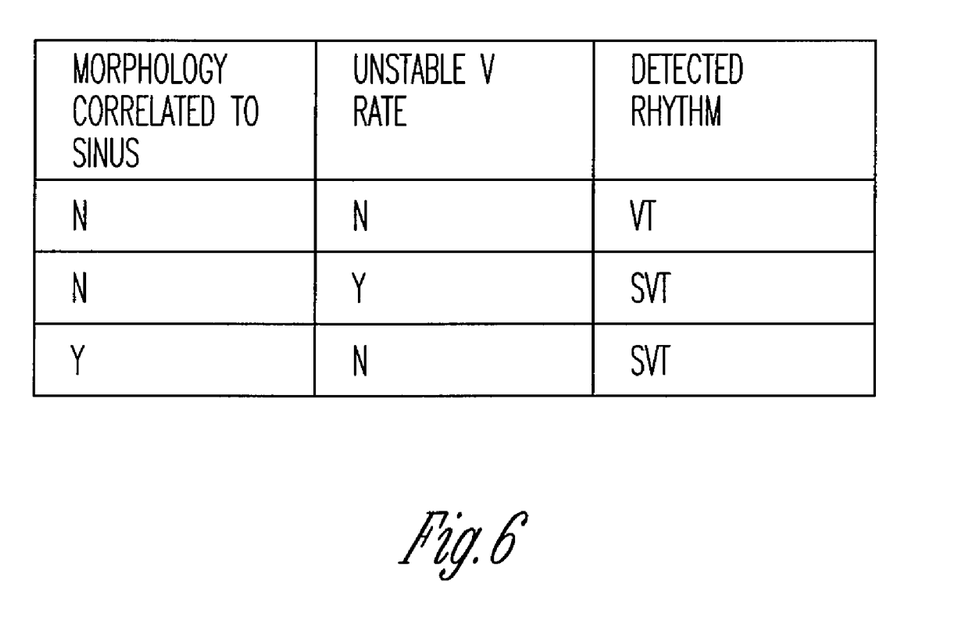
FIG. 6 illustrates a truth table of an exemplary method for combining morphology and rate based criteria yielding an overall SVT/VT discrimination decision for ventricular defibrillators with single chamber (ventricular only) sensing and pacing.

A truth table for an exemplary combined morphology/rate based test for SVT/VT discrimination with single chamber (ventricular only) sensing is shown in FIG. 6. This combined morphology/rate based test employs the criteria of the rate based test so that a tachyarrhythmia is judged as an SVT if the ventricular rate is unstable. The addition of the ventricular stability criterion in the single chamber case allows the option of detecting AF with significant morphological variation if ventricular instability is present. If the ventricular stability criterion is used in the single chamber defibrillator with single chamber sensing, the VT zone should be selected to be below the patient's polymorphic VT rate, since polymorphic VT also exhibits an unstable ventricular response.

In an alternative embodiment, a plurality of electrograms generated by the shock electrode are continuously stored in a rolling onset buffer. Upon detection of a tachyarrhythmia, feature correlation coefficients are computed for the electrograms stored in the onset buffer, and it is determined whether the stored electrograms indicate normally conducted ventricular beats. The combined morphology/rate based test is then used to distinguish between an atrial tachyarrhythmia and a ventricular tachycardia only if a predetermined minimum number of detected events associated with normally conducted ventricular beats are stored in the onset buffer.

In an exemplary method for operating a cardiac rhythm management device that provides post-shock recovery monitoring for tachyarrhythmia discrimination as described above, a first electrogram signal is generated from a cardiac sensing channel. A morphology criterion derived from analysis of the first electrogram signal is then used for discriminating between a supraventricular tachycardia (SVT) and a ventricular tachycardia (VT). The morphology criterion for SVT/VT discrimination is discontinued after delivery of a cardioversion/defibrillation shock, and use of the morphology criterion for SVT/VT discrimination is resumed when a first predetermined minimum number of ventricular beats has been judged as normally conducted. Ventricular beats may be judged as normally conducted or not by utilizing a morphology criterion. The morphology criterion may judge ventricular beats as normally conducted or not by computing a feature correlation coefficient reflecting the extent of correlation between a reference template representing normal ventricular conduction and the first electrogram signal, and judging a ventricular beat as normally conducted if the feature correlation coefficient exceeds a predetermined threshold value. In a particular embodiment, SVT/VT discrimination is performed using a combined morphology/rate based test that includes: a) a rate criterion involving measured atrial and ventricular rates, and b) a morphology criterion, wherein a second predetermined minimum number of normally conducted ventricular beats must be detected during a tachyarrhythmia before an SVT is detected. If a cardioversion/defibrillation shock is delivered, the use of the morphology/rate based test for SVT/VT discrimination is discontinued after delivery of the shock, and a rate based test is substituted therefore. The use of the morphology/rate based test for SVT/VT discrimination is then resumed when the first predetermined minimum number of ventricular beats has been judged as normally conducted following the cardioversion/defibrillation shock.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
one or more sensing channels for sensing cardiac electrical activity and for generating a first electrogram signal;
pulse generation circuitry for delivering pacing pulses and/or shock pulses;
a controller interfaced to the one or more sensing channels and the pulse generation circuitry, wherein the controller is programmed to:
measure a ventricular rate from sensed ventricular electrical activity;
detect a tachyarrhythmia that may be either a supraventricular tachycardia (SVT) or a ventricular tachycardia (VT) if the measured ventricular rate is within a specified range;
discriminate between SVT and VT with a test for SVT/VT discrimination that includes a morphology criterion based on an analysis of the first electrogram signal;
deliver either a cardioversion/defibrillation shock or anti-tachycardia pacing to treat the tachyarrhythmia; and, if a cardioversion/defibrillation shock is delivered:
discontinue use of the morphology criterion in the test for SVT/VT discrimination after delivery of the cardioversion/defibrillation shock for at least one ventricular beat;
judge whether or not one or more ventricular beats that occur after delivery of the cardioversion/defibrillation shock are normally conducted; and,
resume use of the morphology criterion in the test for SVT/VT discrimination when a first predetermined minimum number of ventricular beats occurring after delivery of the cardioversion/defibrillation shock has been judged as normally conducted.

2. The device of claim 1 wherein the controller is programmed to perform the judging as to whether or not one or more ventricular beats that occur after delivery of the cardioversion/defibrillation shock are normally conducted by utilizing a morphology criterion.

3. The device of claim 1 wherein the controller is further programmed to measure an atrial rate from sensed atrial electrical activity and programmed such that:
the test for SVT/VT discrimination is a combined morphology/rate based test that includes: a) a rate criterion involving the measured atrial and ventricular rates, and b) the morphology criterion, wherein the morphology criterion specifies that a second predetermined minimum number of normally conducted ventricular beats must be detected during a tachyarrhythmia before an SVT is detected;
if a cardioversion/defibrillation shock is delivered, the use of the morphology/rate based test for SVT/VT discrimination is discontinued after delivery of the cardioversion/defibrillation shock, and a rate based test is substituted therefore; and,
the use of the morphology/rate based test for SVT/VT discrimination is resumed when the first predetermined minimum number of ventricular beats has been judged as normally conducted following the cardioversion/defibrillation shock.

4. The device of claim 3 wherein the controller is further programmed such that when discriminating between SVT and VT by the combined morphology/rate based test, deeming a tachycardia as SVT if: 1) the measured atrial rate is greater than or equal to the measured ventricular rate, and a predetermined minimum fraction of a specified number of ventricular beats has been judged as normally conducted, or 2) the atrial rate is greater than a preset threshold, the atrial rate is greater than or equal to the ventricular rate, and the ventricular rate is unstable.

5. The device of claim 1 wherein the controller is programmed to perform the judging as to whether or not one or more ventricular beats that occur after delivery of the cardioversion/defibrillation shock are normally conducted by beginning to count normally conducted ventricular beats after a predetermined delay period following delivery of the cardioversion/defibrillation shock.

6. The device of claim 3 wherein the controller is programmed such that, when discriminating between SVT and VT by the rate criterion, a tachycardia is judged as a ventricular tachycardia if the ventricular rate is greater than the atrial rate or the ventricular rate is suddenly increased and stable.

7. The device of claim 3 wherein the controller is programmed such that, when discriminating between SVT and VT by the rate criterion, a tachycardia is judged as an SVT if the atrial rate is greater than a preset threshold, the atrial rate is greater than or equal to the ventricular rate, and the ventricular rate is unstable.

8. The device of claim 5 wherein the predetermined delay period is approximately 10 seconds.

9. The device of claim 1 wherein the controller is programmed to resume use of the morphology criterion following the cardioversion/defibrillation shock if at least one ventricular beat has been judged as normally conducted.

10. The device of claim 1 wherein the controller is programmed to periodically test for a normally conducted ventricular beat following the cardioversion/defibrillation shock and, if a normally conducted ventricular beat is detected, begin to count normally conducted ventricular beats and resume use of the morphology criterion if the first predetermined minimum number of normally conducted ventricular beats are counted.

11. The device of claim 1 wherein the controller is programmed to judge whether a specified minimum fraction of a specified number of ventricular beats occurring after delivery of the cardioversion/defibrillation shock has been normally conducted when judging whether a first predetermined minimum number of ventricular beats occurring after delivery of the cardioversion/defibrillation shock has been normally conducted.

12. The device of claim 3 wherein the controller is programmed to judge ventricular beats as normally conducted or not using the morphology criterion by computing a feature correlation coefficient, the feature correlation coefficient reflecting the extent of correlation between a reference template representing normal ventricular conduction and the first electrogram signal, and judge a ventricular beat as normally conducted if the feature correlation coefficient exceeds a predetermined threshold value.

13. The device of claim 12 further comprising:
a bipolar electrode for generating a second electrogram; and,
wherein the controller is further programmed to compute the feature correlation coefficient for a particular ventricular beat by aligning the first electrogram and the normal conduction template with the second electrogram and computing a correlation coefficient between selected points of the first electrogram and the normal conduction template.

14. The device of claim 1 wherein the controller is programmed to, when delivering a cardioversion/defibrillation shock to treat the tachyarrhythmia, deliver an atrial conversion shock if SVT is detected and delivering a ventricular cardioversion/defibrillation shock if VT is detected.

15. The device of claim 1 wherein the controller is programmed such that the SVT/VT discrimination test is a combined morphology/rate based test that includes: a) a rate criterion involving the measured ventricular rate, and b) the morphology criterion, wherein the morphology criterion specifies that a second predetermined minimum number of normally conducted ventricular beats must be detected during a tachyarrhythmia before an SVT is detected.

16. A cardiac rhythm management device, comprising:
means for delivering a cardioversion/defibrillation shock;
means for generating a first electrogram signal;
means for utilizing a morphology criterion derived from analysis of the first electrogram signal for discriminating between a supraventricular tachycardia (SVT) and a ventricular tachycardia (VT), referred to as SVT/VT discrimination;
means for discontinuing use of the morphology criterion for SVT/VT discrimination after delivery of a cardioversion/defibrillation shock; and, means for resuming use of the morphology criterion for SVT/VT discrimination when a first predetermined minimum number of ventricular beats has been judged as normally conducted.

17. The device of claim 16 wherein ventricular beats are judged as normally conducted by utilizing a morphology criterion.

18. The device of claim 16 further comprising:
means for measuring a ventricular rate from sensed ventricular electrical activity;
means for computing a feature correlation coefficient for selected ventricular beats, the feature correlation coefficient reflecting the extent of correlation between a reference template representing normal ventricular conduction and the first electrogram signal, and judging a ventricular beat as normally conducted if the feature correlation coefficient exceeds a predetermined threshold value;
means for discriminating between SVT and VT by a combined morphology/rate based test which includes: a) a rate criterion involving the measured ventricular rate, and b) a morphology criterion, wherein a second predetermined minimum number of normally conducted ventricular beats must be detected during a tachyarrhythmia before an SVT is detected;
means for detecting a tachyarrhythmia and subsequently restoring normal sinus rhythm with a cardioversion/defibrillation shock;
means for discontinuing use of the morphology/rate based test for SVT/VT discrimination after delivery of the shock and substituting a rate based test therefor; and,
means for resuming use of the morphology/rate based test for SVT/VT discrimination when the first predetermined minimum number of ventricular beats has been judged as normally conducted during the normal sinus rhythm following the cardioversion/defibrillation shock.

19. The device of claim 18 further comprising:
means for measuring an atrial rate from sensed atrial activity; and,
wherein the rate criterion is based upon the measured atrial and ventricular rates.

20. The device of claim 19 wherein the cardioversion/defibrillation shock delivering means includes means for delivering shocks to the ventricles and means for delivering shocks to the atria.

21. The device of claim 19 further comprising:
means for setting a post-shock recovery flag after delivery of a shock;
means for employing the rate based test to distinguish between an atrial tachyarrhythmia and a ventricular tachycardia if the post-shock recovery flag is set;
means for employing the combined morphology/rate based test for SVT/VT discrimination if the post-shock recovery flag is cleared, where a tachycardia is judged as an SVT if: 1) the measured atrial rate is greater than or equal to the measured ventricular rate, and 2) a predetermined minimum fraction of a specified number of ventricular beats has been judged as normally conducted;
means for monitoring ventricular beats during supraventricular rhythm after delivery of a cardioversion/defibrillation shock and clearing the post-shock recovery flag when the first predetermined minimum number of ventricular beats has been judged as normally conducted.

22. The device of claim 21 further comprising means for beginning to count normally conducted ventricular beats after a predetermined delay period following delivery of a shock.

* * * * *